United States Patent
Lee et al.

(10) Patent No.: US 12,404,431 B2
(45) Date of Patent: Sep. 2, 2025

(54) ADHESIVE HYDROGELS AND USES THEREOF

(71) Applicant: The Trustees of The University of Pennsylvania, Philadelphia, PA (US)

(72) Inventors: Daeyeon Lee, Wynnewood, PA (US); Kathleen J. Stebe, Penn Valley, PA (US); Laura Bradley, Amherst, MA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 611 days.

(21) Appl. No.: 16/636,967

(22) PCT Filed: Aug. 6, 2018

(86) PCT No.: PCT/US2018/045358
§ 371 (c)(1),
(2) Date: Feb. 6, 2020

(87) PCT Pub. No.: WO2019/032445
PCT Pub. Date: Feb. 14, 2019

(65) Prior Publication Data
US 2020/0369929 A1     Nov. 26, 2020

Related U.S. Application Data

(60) Provisional application No. 62/541,945, filed on Aug. 7, 2017.

(51) Int. Cl.
| | |
|---|---|
| C09J 133/06 | (2006.01) |
| B01J 13/00 | (2006.01) |
| C08L 33/06 | (2006.01) |
| C08L 33/08 | (2006.01) |
| C08L 33/10 | (2006.01) |
| C08L 101/14 | (2006.01) |
| C09J 133/08 | (2006.01) |
| C09J 133/10 | (2006.01) |

(52) U.S. Cl.
CPC ....... *C09J 133/066* (2013.01); *B01J 13/0065* (2013.01); *C08L 33/06* (2013.01); *C08L 33/066* (2013.01); *C08L 33/08* (2013.01); *C08L 33/10* (2013.01); *C08L 101/14* (2013.01); *C08L 2203/02* (2013.01); *C09J 133/06* (2013.01); *C09J 133/08* (2013.01); *C09J 133/10* (2013.01)

(58) Field of Classification Search
CPC ....... A61K 9/06; A61K 47/32; B01J 13/0052; B01J 13/0065; C08L 33/06; C08L 33/066; C08L 33/08; C08L 33/10; C08L 101/14; C08L 2203/02; C09J 133/06; C09J 133/066; C09J 133/08; C09J 133/10
See application file for complete search history.

(56) References Cited

U.S. PATENT DOCUMENTS

| | | | |
|---|---|---|---|
| 8,701,671 B2 | 4/2014 | Kovarik | |
| 2004/0242770 A1* | 12/2004 | Feldstein | ............... C09J 131/04 525/54.3 |
| 2006/0219143 A1* | 10/2006 | Brennan | ................... E02B 9/06 114/67 R |

FOREIGN PATENT DOCUMENTS

| | | | | |
|---|---|---|---|---|
| WO | WO-9629035 A1 * | 9/1996 | ............. | A61F 13/02 |
| WO | WO-2015055661 A1 * | 4/2015 | ........... | A61L 27/227 |

OTHER PUBLICATIONS

Revzin et al., Fabrication of Poly(ethylene glycol) Hydrogel Microstructures Using Photolithography, 2001, Langmuir, 17, 5440-5447.*

Orakdogen, Design and Synthesis of Dual-Responsive Hydrogels Based on N,N-Dimethylaminoethyl methacrylate by Copolymerization with N-Isopropylacrylamide, 2014, Macromolecular Research, vol. 22, No. 1, pp. 32-41).*

Warner et al., Design and 3D Printing of Hydrogel Scaffolds with Fractal Geometries, ACS Biomater. Sci. Eng. 2016, 2, 1763-1770.*

Bradley et al., "Rough Adhesive Hydrogels (RAd gels) for Underwater Adhesion", ACS Appl. Mater. Interfaces, vol. 9, 2027, pp. 27409-27413.

Gupta et al., "Measurement and Scaling of Hydrodynamic Interactions in the Presence of Draining Channels", Langmuir, 2012, vol. 28, 14703-14712.

\* cited by examiner

*Primary Examiner* — Eli D. Strah
(74) *Attorney, Agent, or Firm* — BakerHostetler

(57) ABSTRACT

Adhesive hydrogels comprising a (co)polymer matrix, wherein the adhesive hydrogel comprises at least one rough surface as well as processes for preparing such hydrogels are disclosed.

12 Claims, 9 Drawing Sheets

ADHESIVE HYDROGELS AND USES THEREOF

CROSS-REFERENCE TO RELATED APPLICATIONS

The present application is the National Stage Application of International Patent Application No. PCT/US2018/045358, filed Aug. 6, 2018, which claims the benefit of provisional U.S. Patent Application No. 62/541,945, filed Aug. 7, 2017, which foregoing applications are fully incorporated herein by reference in their entireties for any and all purposes.

FIELD OF THE INVENTION

The present disclosure relates generally to adhesive hydrogels comprising a (co)polymer matrix, wherein the adhesive hydrogel comprises at least one rough surface. The present disclosure also relates generally to processes for preparing such hydrogels.

BACKGROUND OF THE INVENTION

Advances in wet environment/underwater adhesion have inspired recent studies focused on developing materials capable of such adhesion for biomedical and environmental applications. Most notably, the finding that sea mussels use catechol-moieties to strongly adhere to surfaces in the ocean has led to the development of a variety of catechol-functionalized materials, including hydrogels, polymer cements/glues, and coatings. The distinct advantage of catechol chemistry is the strong adhesion to surfaces with a range of compositions and mechanical properties. However, recent studies show that oxidation of catechol moieties can produce cytotoxic concentrations of reactive oxygen species, such as hydrogen peroxide, potentially limiting their biocompatibility.

For biomedical applications, wet environment/underwater adhesives need to be biocompatible and complementary to soft, wet biological tissues or biomimetic hydrogels. Current alternatives to catechol-based adhesives for biomaterials typically require harsh conditions, such as chemical reaction, heat, light exposure, or non-physiological pH. It is thus desirable to develop adhesion schemes that do not require harsh conditions or invoke cytotoxic responses.

Recently, nanoparticle solutions have been used to adhere hydrogels and biological tissues. Nanoparticles facilitate adhesion by adsorption of the hydrogel or tissue matrix to the particle surface so that particles bridge the two substrates. Nanoparticles, however, have not been shown to enable adhesion between substrates with pronounced differences in mechanical properties (i.e., between hard and soft surfaces), which is often necessary to implant medical devices in vivo (e.g., the electrodes of neurostimulator devices). Biocompatible adhesives that are compatible to substrates of different chemistries and mechanical properties are critical to universal use in vivo.

Thus, there exists a continuing need for improved adhesives that can be used effectively in wet environments and underwater.

EMBODIMENTS OF THE INVENTION

This need is met by the adhesive hydrogels of the present invention.

One embodiment of the present invention is an adhesive hydrogel comprising a (co)polymer matrix, wherein the adhesive hydrogel comprises at least one rough surface.

In certain embodiments, the adhesive hydrogel according to the present invention further comprises at least one smooth surface. In certain embodiments, the adhesive hydrogel according to the present invention comprises two rough surfaces. In certain of these embodiments, each of the two rough surfaces are situated on opposite sides of the adhesive hydrogel to each other. In certain embodiments, the root mean square roughness of the at least one rough surface is at least one order of magnitude higher than the root mean square roughness of the at least one smooth surface.

In certain embodiments, the (co)polymer matrix of the adhesive hydrogel according to the present invention comprises a biocompatible (co)polymer. In certain of these embodiments, the biocompatible (co)polymer is a homopolymer or copolymer of 2-hydroxyethyl methacrylate. In certain embodiments, the biocompatible (co)polymer is a copolymer of 2-hydroxyethyl methacrylate and poly(ethylene glycol) diacrylate.

Another embodiment of the present invention is a process for preparing the adhesive hydrogel according to the present invention, comprising the steps of (1) providing a reaction mixture comprising at least one monomer and water, (2) charging a container comprising a smooth interior surface with a volume of the reaction mixture, such that the volume of the reaction mixture is less than the volume of the container, and (3) covering the charged container with a lid and polymerizing the at least one monomer in the presence of the water to obtain the adhesive hydrogel comprising at least one rough surface and at least one smooth surface.

Yet another embodiment of the present invention is a process for preparing the adhesive hydrogel according to the present invention, comprising the steps of (1) providing a reaction mixture comprising at least one monomer and water, (2) charging a container comprising a rough interior surface with a volume of the reaction mixture, such that the volume of the reaction mixture is less than the volume of the container, and (3) covering the charged container with a lid and polymerizing the at least one monomer in the presence of the water to obtain the adhesive hydrogel comprising two rough surfaces.

DETAILED DESCRIPTION OF THE INVENTION

Figure 1A:
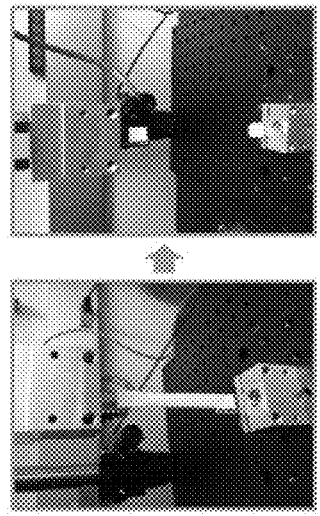
FIG. 1A depicts load-extension curves for adhesive hydrogels according to the present invention adhered underwater at both ends to polydimethylsiloxane compared to a neat hydrogel (not adhered to polydimethylsiloxane).

In one aspect of the present invention, the present disclosure provides for novel adhesive hydrogels comprising a (co)polymer matrix, wherein the adhesive hydrogel comprises at least one rough surface. These adhesive hydrogels exhibit adhesion to both hard and soft substrates in both wet (including underwater and in non-aqueous liquid environments, such as hexadecane and glycerol) and dry environments. This adhesion is attributable to the surface topography of the at least one rough surface of the adhesive hydrogel at its interface with the substrate, the at least one rough surface being characterized by a "peak/canyon" topography. This surface topography can be random or structured (i.e., have pattern(s)). The peaks form adhesion sites to the substrate, while the valleys form a network of microchannels that allow fluids, such as water, to drain from between the contact points between the substrate and the adhesive hydrogel, resulting in drying of the contact area, which, in turn, further promotes adhesion between the materials, even in wet environments. This is surprising, since surface roughness is typically considered detrimental to adhesion in dry environments.

In certain embodiments, the adhesive hydrogels according to the present invention may further comprise at least one smooth surface or may comprise two rough surfaces. In embodiments where the adhesive hydrogels according to the present invention comprise two rough surfaces, each of the two rough surfaces may be situated on opposites sides of the adhesive hydrogel to each other. In certain other embodiments, the adhesive hydrogels are in the form of patches or particles.

In certain embodiments, the (co)polymer matrix of the adhesive hydrogels according to the present invention may comprise any (co)polymer(s) suitable for forming a hydrogel. In certain embodiments, the (co)polymer matrix may comprise at least one biocompatible (co)polymer. Examples of such biocompatible (co)polymers include, but are not limited to, homopolymers and copolymers of 2-hydroxyethyl methacrylate, homopolymers and copolymers of poly(ethylene glycol) diacrylate, poly(ethylene oxides) and copolymers thereof, poly(propylene oxides) and copolymers thereof, poly(acrylic acids) and copolymers thereof, poly(vinyl alcohols) and copolymers thereof, and polysaccharide-based (co)polymers. Examples of copolymers of 2-hydroxyethyl methacrylate include, but are not limited to, copolymers of 2-hydroxyethyl methacrylate with poly(ethylene glycol) diacrylate. In certain embodiments, the (co)polymer matrix may comprise at least one (co)polymer that is not biocompatible. Examples of such non-biocompatible (co)polymers include, but are not limited to, homopolymers and copolymers of N-isopropyacrylamide 2-(dimethylamino)ethyl methacrylate.

In certain embodiments, the rough side(s) of adhesive hydrogels according to the present invention can be adhered to a variety of substrates with different compositions and mechanical properties. Examples of such substrates include, but are not limited to, tissue, such as bone and tendon, the rough or smooth surfaces of other hydrogels (e.g., hydrogels based on copolymers of 2-hydroxyethyl methacrylate with poly(ethylene glycol) diacrylate), polystyrene (e.g., Petri dishes), polydimethylsiloxane, carbon steel (e.g., razor blades), titanium, ceramics, parylene, and glass coated with fluorinated silane. The adhesion to polystyrene can also be achieved in either PBS buffer or at elevated temperature (e.g., 80° C.). As such, the adhesive hydrogels according to the present invention may be used in variety of applications, including, but not limited to, biomedical, industrial, and environmental applications. Specific examples of such applications include, but are not limited to, biomedical adhesives, industrial adhesives, bandages, wound repair, contact lenses, surgery, surgically implanted medical devices, and drug delivery. In certain embodiments, the substrate may optionally be pre-treated prior to application of the adhesive hydrogels according to the present invention, but this is not required in most circumstances.

In certain embodiments, adhesion of the adhesive hydrogels according to the present invention to a particular substrate in a dry environment, wet environment, or underwater may be achieved by pressing the adhesive hydrogel to the substrate for twenty seconds using a force of at least 10 N, and then allowing the interface between the adhesive hydrogel and the substrate to set for five minutes.

The (co)polymer of the polymer matrix of the adhesive hydrogel according to the present invention can be present in the adhesive hydrogel in any suitable concentration. In certain embodiments, such suitable concentrations will be dependent on the composition of the (co)polymer. In certain embodiments, the (co)polymer concentration can be less than 32 weight %, based on the total weight of the adhesive hydrogel. In certain other embodiments, the (co)polymer concentration can be in the range of from 28 to 32 weight %, based on the total weight of the adhesive hydrogel.

In certain embodiments, the root mean square roughness of the at least one rough surface of the adhesive hydrogels according to the present invention is at least one order of magnitude higher than the root mean square roughness of the at least one smooth surface. The contributions of the surface and bulk properties to the adhesion of embodiments of the adhesive hydrogels according to the present invention are not independent. The surface features on embodiments of the adhesive hydrogels according to the present invention (approximately 100 μm) are, in certain embodiments, an order of magnitude larger than features used in biomimetic surfaces (~10 μm).

In certain embodiments, adhesive hydrogels according to the present invention can also be adhered to substrates in non-aqueous environments. For example, adhesive hydrogels according to the present invention can be adhered to polystyrene in glycerol and hexadecane. Successful adhesion in glycerol demonstrates that adhesive hydrogels according to the present invention allow fluid drainage in viscous fluid environments. This may be attributable to two effects: (1) the large surface features are expected to aid drainage and (2) a miscible glycerol/water front may reduce the local viscosity of the fluid, as well as change the properties of the hydrogel. Successful adhesion in hexadecane indicates miscibility between the hydrogel and fluid environment is not required. When pressure is applied to the hydrogels, water is expelled, which would surround the gels in a hexadecane environment. In certain embodiments, adhesion in immiscible systems can be used to compare drainage of the fluid environment and drainage of expelled liquid from hydrogels.

Figure 1C:
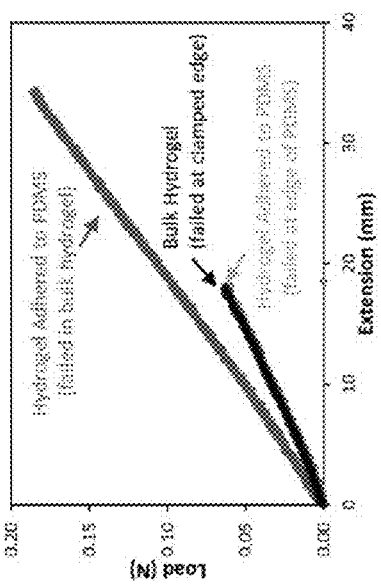
FIG. 1C depicts an adhered adhesive hydrogel according to the present invention breaking at an edge of one polydimethylsiloxane substrate.
Figure 1B:
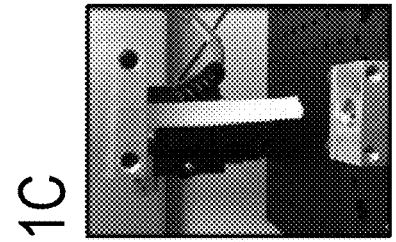
FIG. 1B depicts an adhered adhesive hydrogel according to the present invention breaking within the bulk.
Figure 1B:
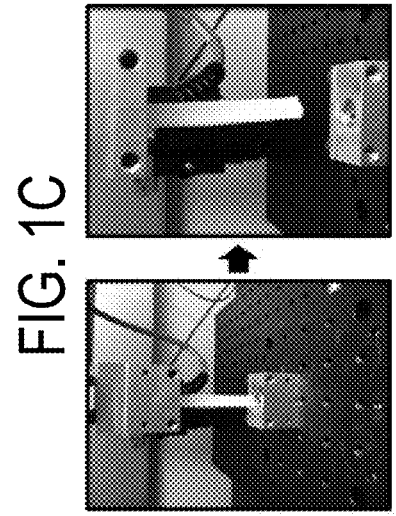
Figure 1D:
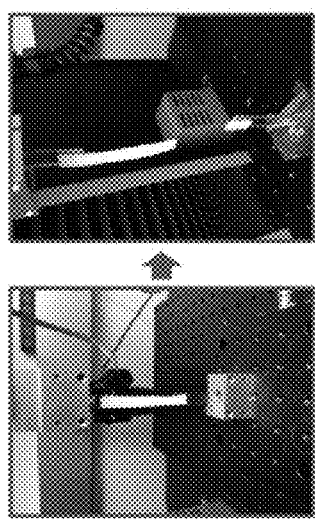
FIG. 1D depicts a non-adhered adhesive hydrogel according to the present invention breaking at a clamped edge.
Figure 2E:
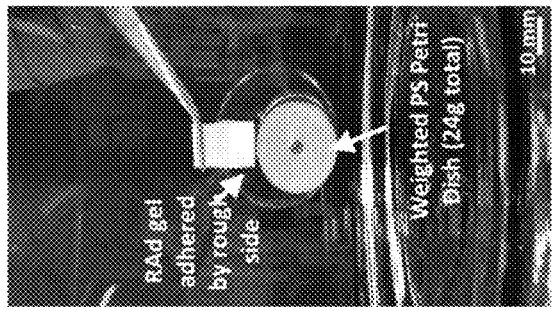
FIG. 2E depicts adhesive hydrogels according to the present invention adhered underwater by the rough side lifting a weighted polystyrene Petri dish.
Figure 9A:
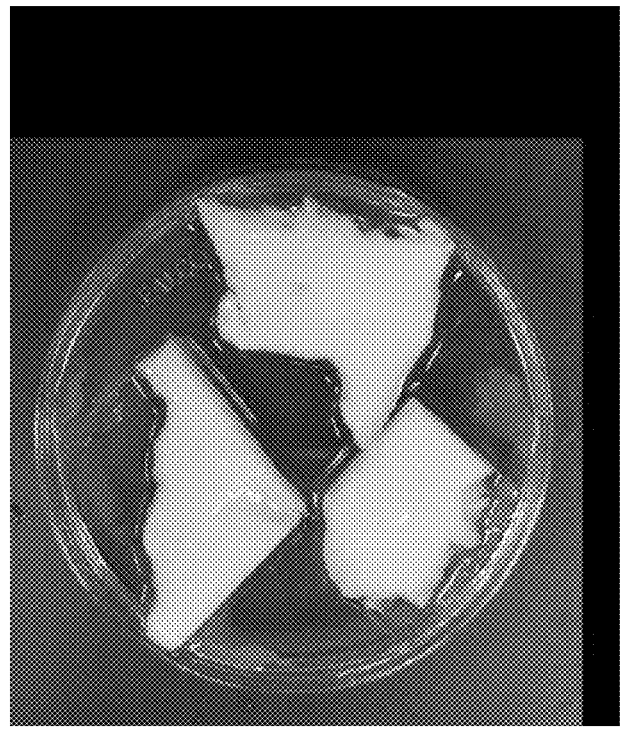
FIG. 9A depicts an image after tweezers were used to try to peel adhesive hydrogels according to the present invention off the surface of a polystyrene Petri dish after the rough side of the adhesive hydrogels was adhered under water to the polystyrene Petri dish.
Figure 9B:
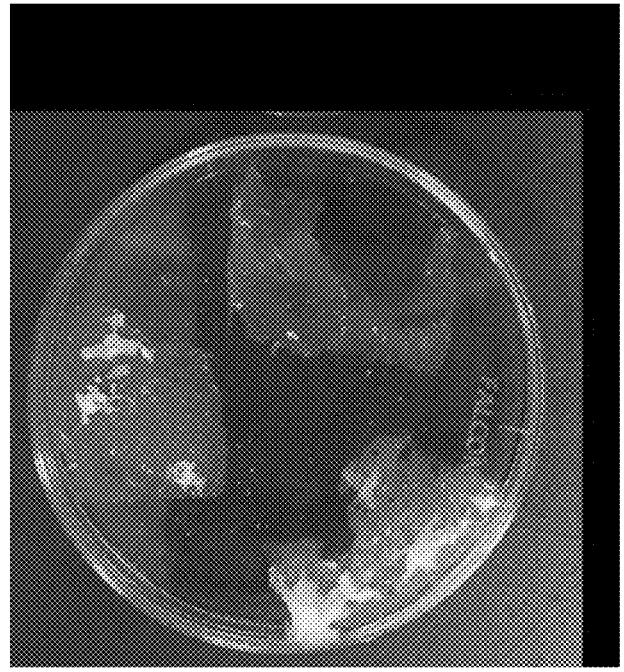
FIG. 9B depicts an image after adhesive hydrogels according to the present invention were rubbed off the surface of a polystyrene Petri dish and a residual layer of hydrogel remains adhered after the rough side of the adhesive hydrogels was adhered under water to the polystyrene Petri dish.

In certain embodiments, the lower bound for the shear adhesion strength of adhesive hydrogels according to the present invention is estimated from single lap shear tests on adhesive hydrogels adhered to polydimethylsiloxane to be 1.8 kPa. Certain embodiments of adhesive hydrogels according to the present invention do not exhibit adhesive failure and instead break at the edge of the adhered area or within the bulk (FIGS. 1A through 1D). See also FIGS. 9B and 9B. The ability of certain embodiments of the adhesive hydrogels according to the present invention to lift a weighted polystyrene Petri dish (adhered area of 1 $cm^2$; total weight of 24 g) suggests a higher minimum for the shear adhesion strength of 2.4 kPa (FIG. 2E). The estimated adhesion strength on the order 1 kPa is the same magnitude as previously reported for nanoparticle adhesives and lower than that of catechol-based systems.

Figure 3A:
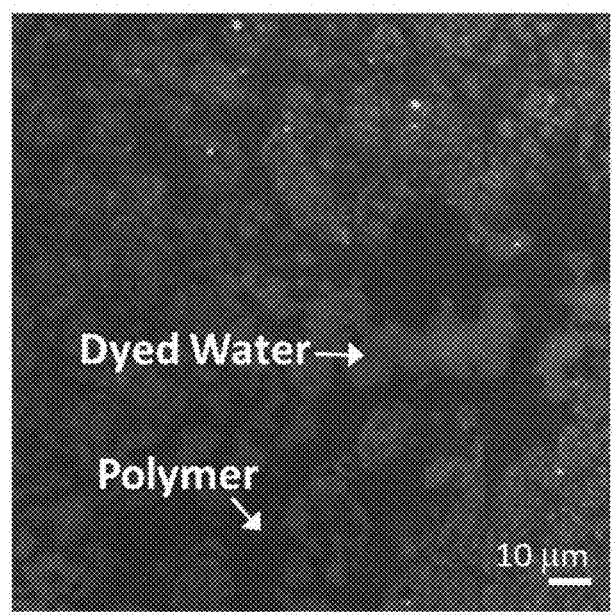
FIG. 3A depicts a confocal image of the adhered interface between a rough surface of an adhesive hydrogel according to the present invention and a polystyrene Petri dish.
Figure 8:
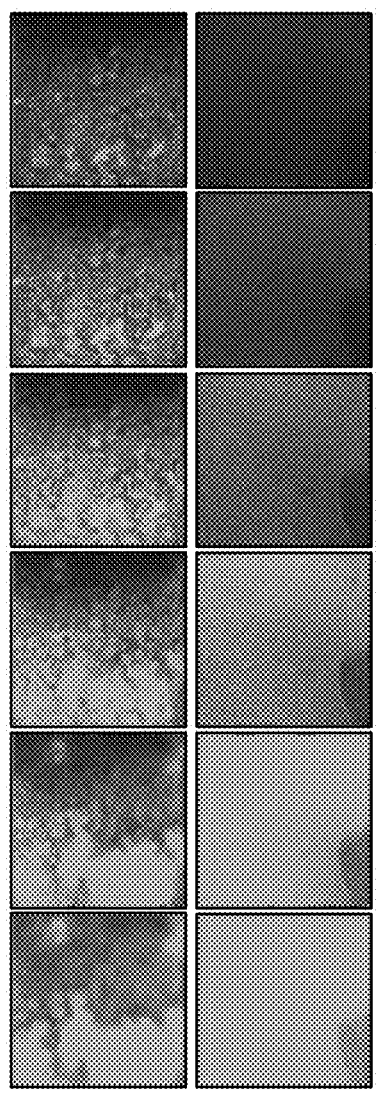
FIG. 8 depicts frames from confocal scans to visualize the hydrogel surface topography.
Figure 8:
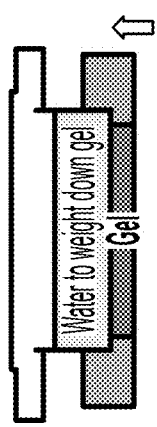

The mechanism that allows the rough surface of the adhesive hydrogels according to the present invention to achieve underwater adhesion was studied by investigating the mode of contact between certain embodiments of the adhesive hydrogel and a substrate. Confocal microscopy images of the rough surface of the adhesive hydrogel according to the present invention pressed to a polystyrene Petri dish containing dyed water indicate that large patches of polymer adhere, trapping water between these features (FIG. 3A). See also FIG. 8 (the distance between the frames is 10 μm and all frames are 1.25 mm×1.25 mm. Adhesion was performed in a water bath dyed with fluorescein sodium salt (green). The rough topography facilitates liquid drainage through interconnected valleys to enable the peaks to make contact with the Petri dish. Fluid drainage in this system is analogous to drainage during the approach of a structured surface to a flat substrate in a liquid environment. During approach, there is a transition from fluid flowing radially to draining through surface networks. Scaling analysis by Gupta and Frechette ("Measurement and Scaling of Hydrodynamic Interactions in the Presence of Draining Channels," Langmuir, Vol. 28, pp. 14703-14712 (2012)) reports that the onset of fluid drainage cannot be correlated to a single length scale describing the surface structure. The toe pad of torrent tree frogs offers an example from nature of how structured surfaces comprised of densely packed polygonal epithelial cells (10-15 μm wide, spaced approximately 1 μm apart) achieve adhesion in flooded conditions due to fluid drainage.

Figure 3B:
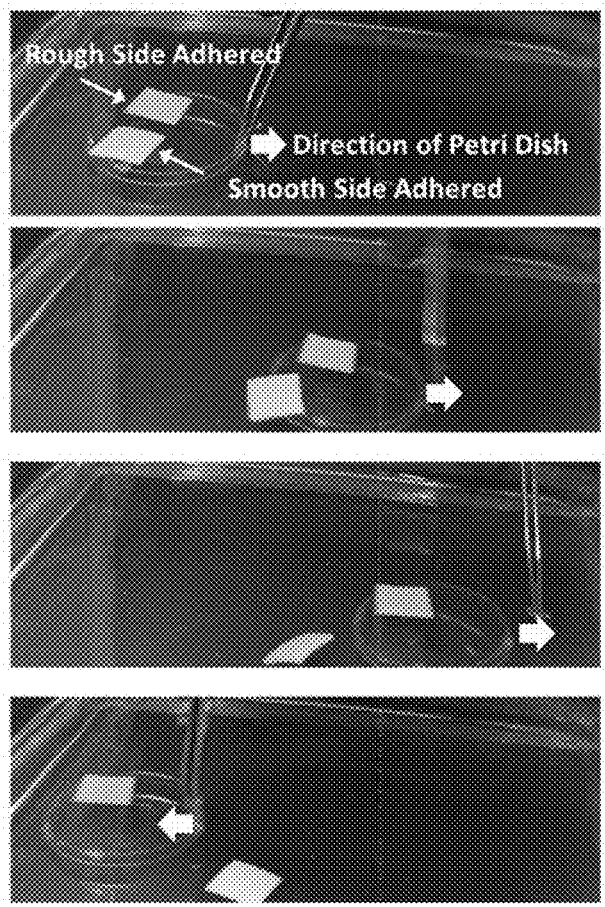
FIG. 3B depicts a series of images depicting underwater adhesion of the surfaces of adhesive hydrogels according to the present invention to a polystyrene Petri dish under shear.

In contrast to the rough surface, when the smooth surface of these embodiments of the adhesive hydrogel according to the present invention are pressed to contact a Petri dish, the hydrogel delaminates and floats in solution. Pressing the smooth surface of the adhesive hydrogel onto the polystyrene substrate underwater traps a liquid layer which prevents two surfaces from making intimate contact for adhesion. The difference in contact is also observed by adhering the two adhesive hydrogel surfaces to a polystyrene Petri dish and then dragging the Petri dish through the water bath (FIG. 3B). As the Petri dish is moved through the water bath, the adhesive hydrogel adhered by the smooth side slips off, whereas the adhesive hydrogel adhered by the rough side remains attached. The adhesive hydrogel adhered by the smooth side delaminates due to a lubricating liquid layer between the hydrogel and the polystyrene. In contrast, the adhesive hydrogel adhered using the rough side remains secured to the Petri dish, even after increasing agitation.

Without being bound by theory, the wet environment adhesion of the adhesive hydrogels according to the present invention may be attributable to two features. The surface roughness of the adhesive hydrogels promotes contact with substrates by facilitating drainage of liquid, while the chemistry of adhesion occurs through interactions between the polymer backbone and substrate. Due to the wettability and compositions of the adhered substrates, hydrogen bonding and electrostatics can be eliminated as potential interactions facilitating adhesion. Hydrophobic interactions are probably relevant and Van der Waals attractions may also play a role. It has been found that the rough surface of the adhesive hydrogel according to the present invention can adhere to substrates with receding contact angles of ≥50°, whereas there is no adhesion on fully water-wetting glass surfaces (i.e., a water receding contact angle of approximately 0°) (Table 2).

In another aspect of the present invention, the present disclosure provides for novel processes for preparing the adhesive hydrogels according to the present invention.

In one embodiment, the process for preparing an adhesive hydrogel comprising at least one rough surface and at least one smooth surface comprises the steps of (1) providing a reaction mixture comprising at least one monomer and water, (2) charging a container comprising a smooth interior surface with a volume of the reaction mixture, such that the volume of the reaction mixture is less than the volume of the container and (3) covering the charged container with a lid and polymerizing the at least one monomer in the presence of the water to obtain the adhesive hydrogel.

Figure 2C:
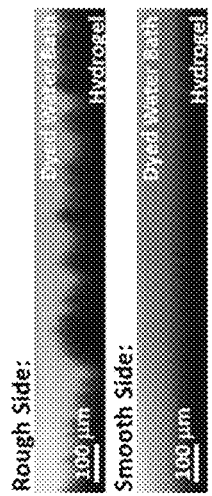
FIG. 2C depicts images of the top (vapor) and bottom (glass) sides of adhesive hydrogels according to the present invention.
Figure 2D:
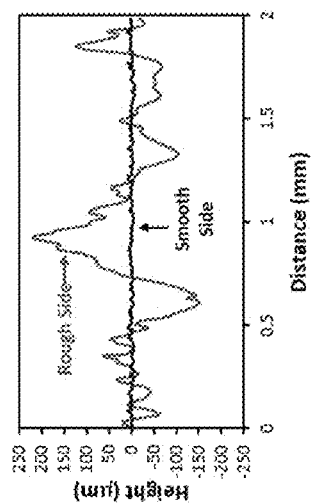
FIG. 2D depicts profilometry scans of the topography of an adhesive hydrogel according to the present invention collected on Smooth-On molds.
Figure 2A:
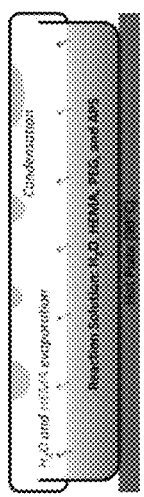
FIG. 2A depicts the cross-section confocal microscopy stacks of the rough and smooth sides of an adhesive hydrogel according to the present invention immersed in a water bath containing fluorescein sodium salt (green).
Figure 2B:
FIG. 2B depicts a schematic of synthesis of an adhesive hydrogel according to the present invention in an open-face set-up comprised of a glass Petri dish and lid.
Figure 6:
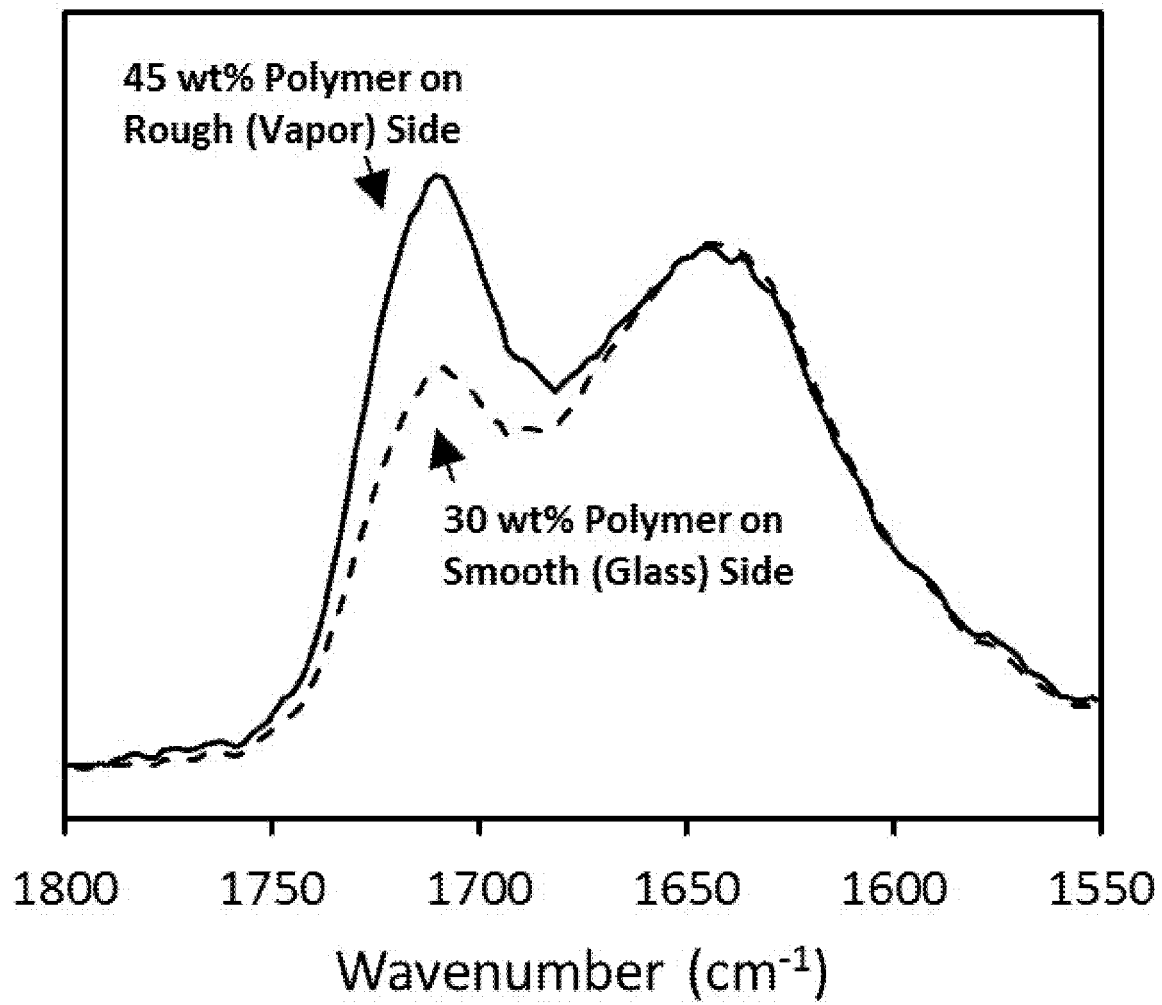
FIG. 6 depicts an ATR-FTIR spectra comparing the composition of the smooth (glass) and rough (vapor) sides of an adhesive hydrogel according to the present invention.

In one embodiment, the hydrogel matrix is comprised of poly(2-hydroxyethyl methacrylate)-co-poly(ethylene glycol) diacrylate (i.e., PHEMA-co-PEGDA), synthesized by a thermally initiated free-radical mechanism in an open-face set-up by polymerizing the reaction solution containing water, monomer (HEMA and PEGDA), and initiator (ammonium persulfate) in a glass Petri dish with a lid. The reaction solution does not fill the entire volume of the Petri dish, leaving an air gap above the liquid. Polymerization in this open-face set-up produces a rough surface on the top side that is in contact with the air gap and a relatively smooth surface on the bottom side that is in contact with the glass Petri dish (FIGS. 2A and 2B). During polymerization, the air gap enables evaporation (primarily of water and a small amount of HEMA), which results in the top (vapor) side of the adhesive hydrogel having a higher concentration of polymer (45 weight % polymer) compared to the bottom (glass) side (30 weight % polymer). (FIG. 6).

Figure 5A:
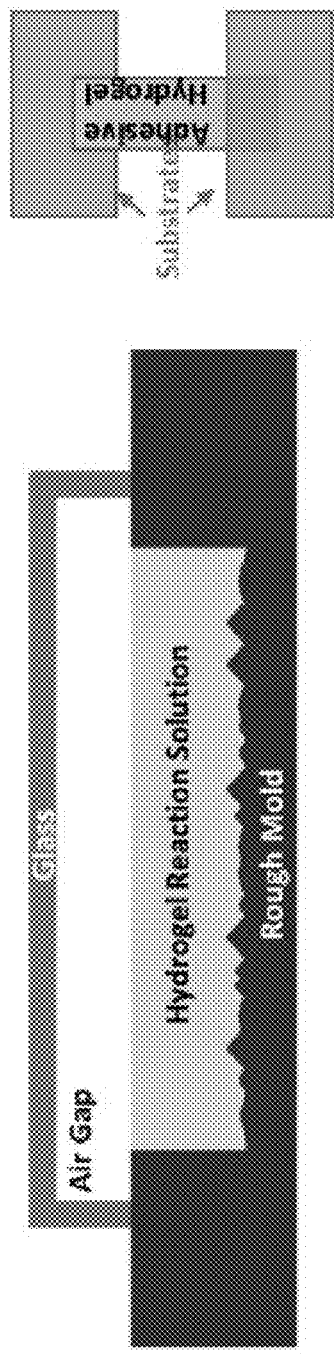
FIG. 5A depicts a schematic of the open-face set-up to synthesize double-sided adhesive hydrogels according to the present invention.
Figure 5A:
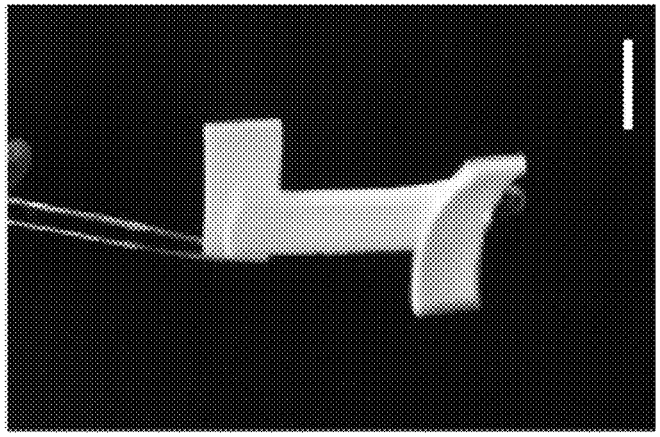
Figure 5B:
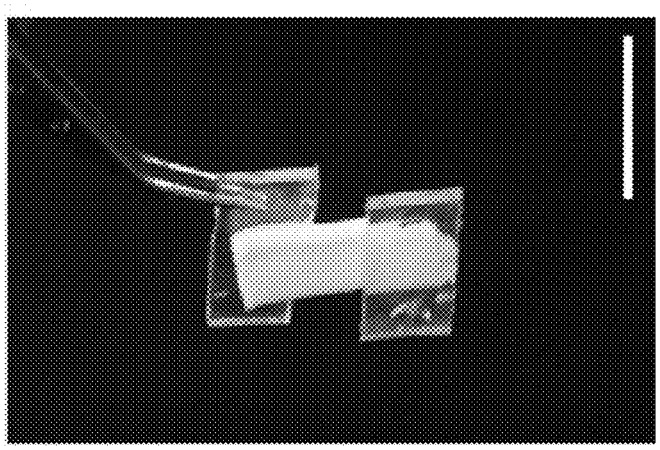
FIG. 5B depicts a schematic of the tethered configuration for testing double-sided adhesion.
Figure 5C:
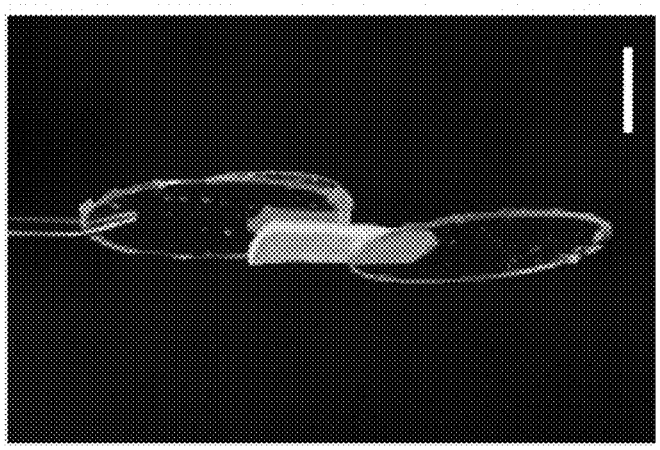
FIG. 5C depicts images of double-sided adhesive hydrogels according to the present invention as tethers for adhering polystyrene (left), polydimethylsiloxane (middle), and non-adhesive hydrogels (right). Scale bars are 25 mm.

In another embodiment, the process for preparing an adhesive hydrogel comprising two rough surfaces comprising the steps of (1) providing a reaction mixture comprising at least one monomer and water, (2) charging a container comprising a rough interior surface with a volume of the reaction mixture, such that the volume of the reaction mixture is less than the volume of the container, and (3) covering the charged container with a lid and polymerizing the at least one monomer in the presence of the water to obtain the adhesive hydrogel. In certain embodiments, the rough interior surface is an integrated part of the container. In certain other embodiments, the rough interior surface can be a mold having a rough surface that is placed in the container, for example, as a bottom surface (FIG. 5A). In certain embodiments, the topography of the rough interior surface of the container, whether integrated or installed as a removable mold, can be random or structured, i.e., have pattern(s). Such double rough-sided adhesive hydrogels according to the present invention can perform underwater adhesion to tether polystyrene, polydimethylsiloxane, or non-adhesive hydrogel substrates (FIGS. 5B and 5C). The adhesion is robust enough to withstand bending and folding of the adhesive hydrogel tether.

The following examples are included to demonstrate preferred embodiments. It should be appreciated by those of skill in the art that the techniques disclosed in the examples which follow represent techniques discovered by the inventor to function well in the practice of the products, compositions, and methods described herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

EXAMPLES

Example 1—Hydrogel Synthesis and Characterization

2-Hydroxyethyl methacrylate ("HEMA"; Sigma-Aldrich; ≥99%), poly(ethylene glycol) diacrylate ("PEGDA"; Sigma Aldrich; average Mn=575), ammonium persulfate ("APS"; Sigma Aldrich; 98%), and deionized water (18 MΩ-cm) were all used as received. The hydrogel reaction solution was prepared by mixing 3.55 mL HEMA, 0.35 mL PEGDA, 11.1 mL H$_2$O, and 0.09 g APS. The total solution volume of 15 mL was added to a glass Petri dish (100×20 mm) and covered with a glass lid. The Petri dish was then placed on a hotplate at 90° C. and polymerized for 20 minutes. After polymerization, the hydrogel was removed from the Petri dish, placed in a water bath for 24 hours, and then subsequently transferred to a fresh water bath for storage. The hydrogels in Table 1 were synthesized by changing the ratio of water to monomer at fixed HEMA/PEGDA ratio of 10/1 v/v and 1 weight % APS (relative to monomer). Table 1 summarizes the adhesive property of hydrogels as a function of gel composition and surface topography.

TABLE 1

Adhesive Behavior of Hydrogels as a Function of Composition and Surface Topography.

| Polymer Weight % | Smooth Surface | Rough Surface |
|---|---|---|
| 23 | Not Adhesive | Adhesive |
| 28* | Not Adhesive | Adhesive |
| 32 | Not Adhesive | Not Adhesive |
| 45 | Not Adhesive | Not Adhesive |

* denotes the original recipe for the hydrogels previously discussed in detail.

The polymer concentration of the hydrogel surface was analyzed by attenuated total reflectance Fourier transform infrared spectroscopy (ATR-FTIR) on a Nicolet 6700 instrument. Spectra were collected using 64 scans between 600-4000 cm$^{-1}$ with a step size of 4 cm$^{-1}$. The polymer concentration is determined by the relative intensity of the polymer carbonyl peak at 1711 cm$^{-1}$ and the water —OH bending at 1653 cm$^{-1}$. As shown in FIG. 6, the rough side of the hydrogel that was exposed to the air interface during polymerization displayed a higher polymer concentration than the smooth side formed at the glass interface.

Confocal scans of the hydrogel surface topography were collected on an Olympus FV1000 instrument using a 10× objective with a step size of 3 μm in the z-direction. Fluorescein sodium salt is used to dye the water bath and imaged using an excitation of 488 nm and emission of 515 nm. As shown in FIG. 2C, confocal microscopy of the hydrogel immersed in a dyed water bath illustrates the difference in surface roughness of the two sides. The cross-sectional images in FIG. 2C were compiled using the Volume Viewer plugin in Fiji Software.

Receding contact angles were measured on an Attension Theta goniometer using the withdraw method. Table 2 lists the receding contact angle and observed adhesive behavior of the rough side of the hydrogel to tested substrates:

TABLE 2

| Substrate | Receding Contact Angle (°) | Adhesive Behavior of Hydrogel Rough Side |
|---|---|---|
| Fluorinated Silane-Coated Glass | 95 ± 2 | Adhesive |
| PDMS | 79 ± 4 | Adhesive |
| Polystyrene | 61 ± 2 | Adhesive |
| Carbon Steel Razor Blade | 51 ± 9 | Adhesive |
| Untreated Glass | 0 | Not Adhesive |

Example 2—Molds of the Hydrogel Surface Topography

Figure 4:
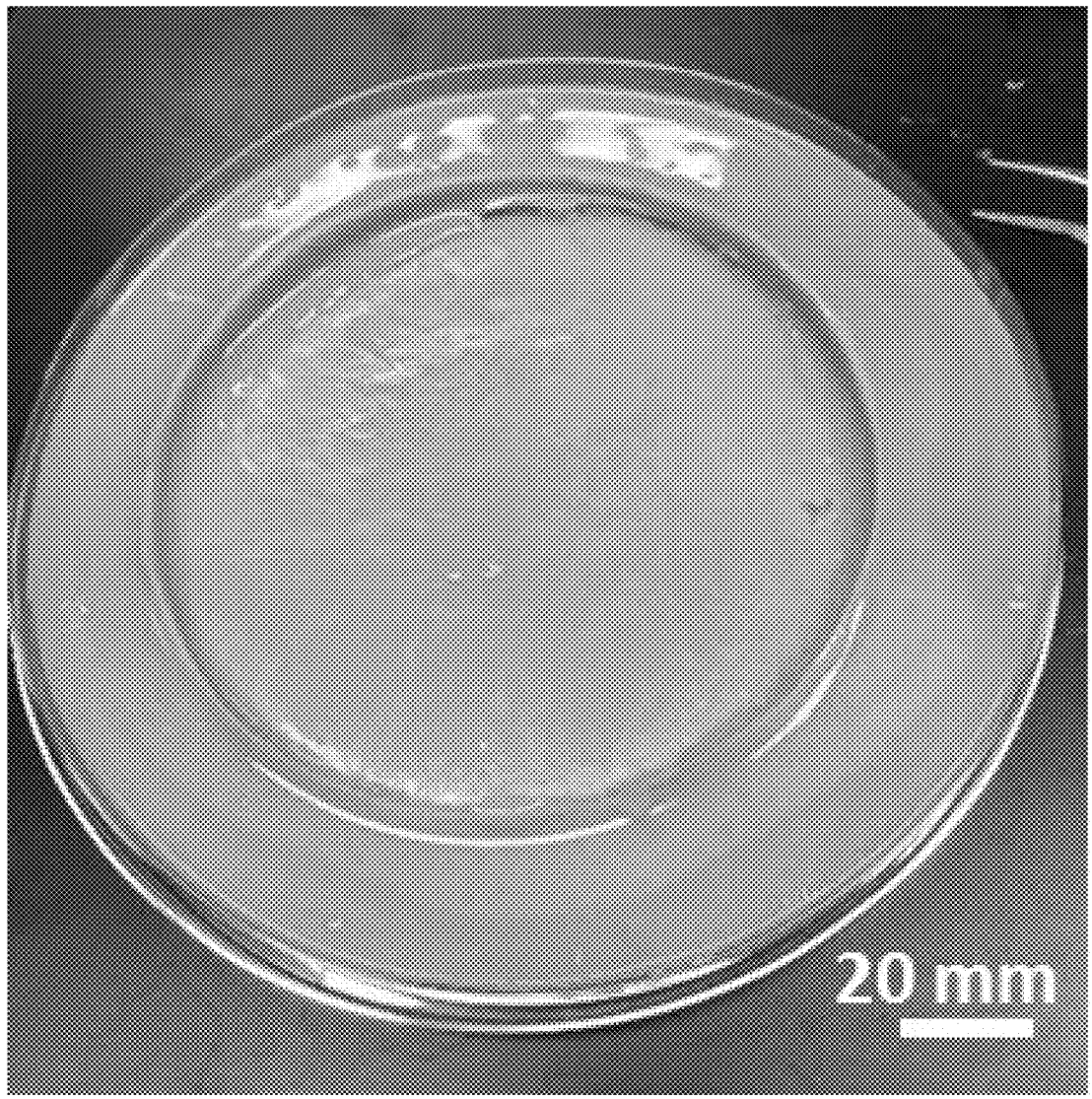
FIG. 4 depicts a photograph of a Smooth-On mold of the rough side of an adhesive hydrogel according to the present invention.

To quantify the root mean square (RMS) roughness, the top and bottom surfaces of a RAd gel were molded using a silicone elastomer (Smooth-On Mold Star). Molds of the hydrogel surface topography were prepared using Smooth-On Mold Star 16 Fast. The hydrogels were removed from water baths and Kim Wipes were used to dry excess water off the surface. As shown in FIG. 4, the Smooth-On mixture was then spread on the surface of the hydrogels and cured at room temperature for 30 minutes. A P-7 Stylus Profiler was used to measure the surface topography on the molds of the hydrogels. Scans are performed using a length of 1980 µm, a speed of 50 µm/sec, and a force of 0.5 mg. As shown in FIG. 2D, profilometry on these molds measured RMS roughnesses (1.98 mm scan length) of 73±3 µm and 4±1 µm for the rough (top) and smooth (bottom) sides, respectively.

Example 3—Cell Adhesion and Viability

Figure 7:
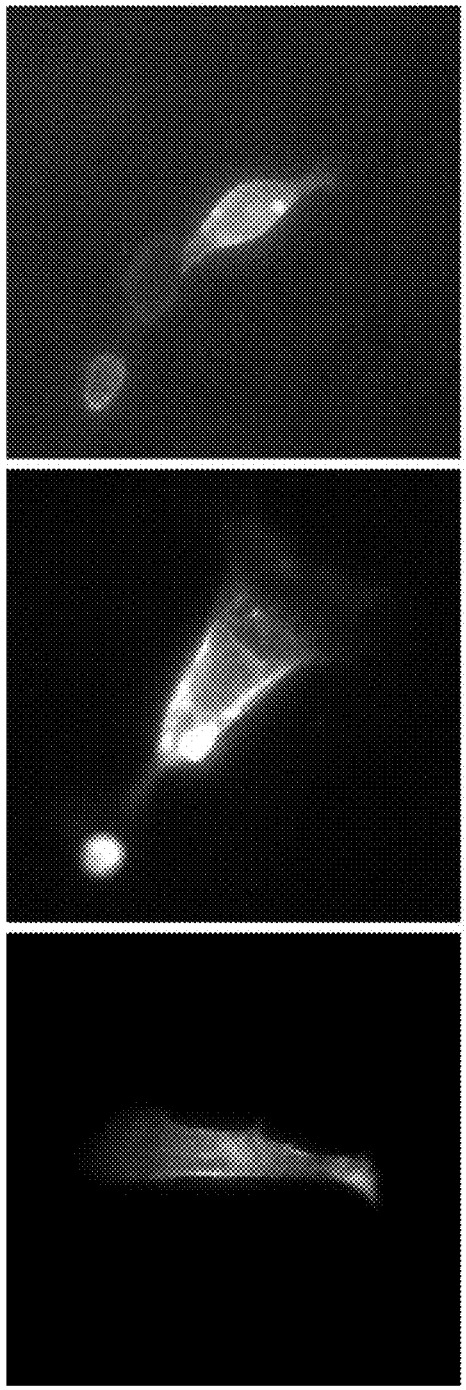
FIG. 7 depicts fluorescent microscopy images of LifeAct-RFP mouse embryonic fibroblasts seeded on hydrogels according to the present invention and imaged after 23 hours.
Figure 7:
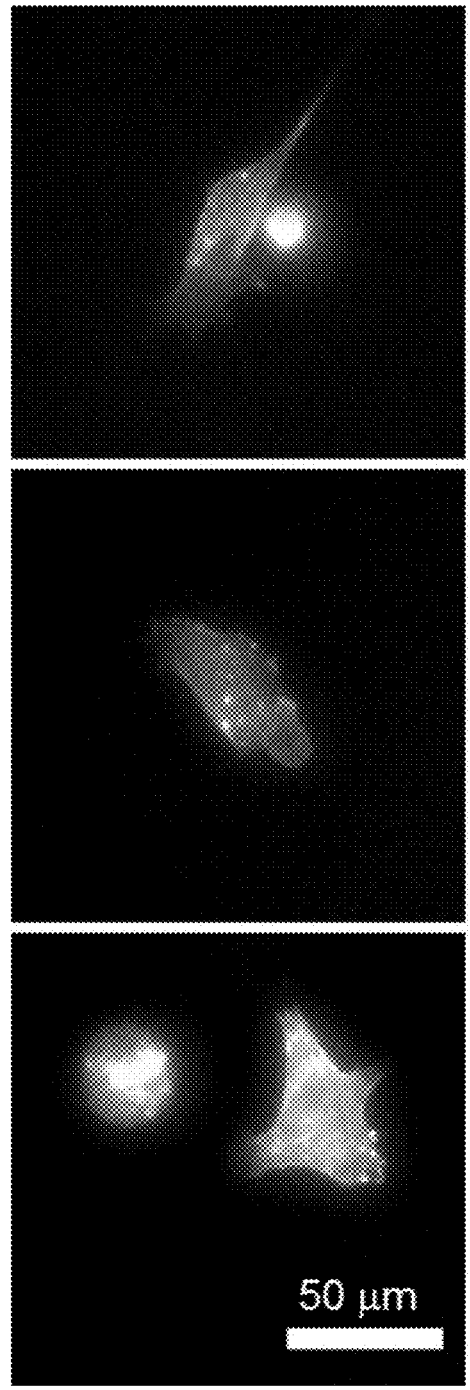

To determine the biocompatibility of the hydrogels according to the present invention, immortalized mouse embryonic fibroblasts (MEFs) are infected with LifeAct-RFP adenoviral vector, seeded on the hydrogel surface, and monitored for viability. Hydrogels (1 cm$^2$) are placed in 35 mm Petri dishes and incubated with MEF medium containing 10 volume % fetal bovine serum, 2 mM L-glutamine, 2.5 µM HEPES, and 50 µg/mL gentamicin for 90 minutes in the presence of 10% $CO_2$ at 37° C. The hydrogels are then seeded at 3000 cells/cm$^2$ and incubated at 37° C. and 10% $CO_2$ for 23 hours. After incubation, the cells are imaged using a Nikon Eclipse 80i epifluorescence microscope. The cells express LifeAct-RFP, a fluorescent F-actin-binding protein. As shown in FIG. 7, imaging of LifeAct-RFP showed that cells attach and spread on both sides of the hydrogels, demonstrating viability.

Example 4—Single Lap Shear Test

Lap shear tests of the hydrogels were performed on a standard tension testing machine (MTS Criterion Model 43). The rough side of hydrogels (7 mm width×1 mm thickness×70 mm length) were adhered underwater to PDMS using an overlap distance of 10 mm on both ends. This set-up avoids having to clamp the hydrogel into the instrument. The specimens were tested to failure using a displacement controlled test at a rate of 10 mm/min. FIG. 1A displays force-extension curves for two adhered hydrogel samples compared to a bulk hydrogel (not adhered to PDMS and clamped directly into the instrument). As shown in FIG. 1B, one of the adhered hydrogel samples demonstrates failure within the bulk indicating the adhesive strength is greater that the strength of the hydrogel. Interestingly, the behavior of the second adhered hydrogel and the bulk hydrogel are identical; both fail at one end of the sample. As shown in FIGS. 1C and 1D respectively, the adhered hydrogel fails at the edge of the PDMS and the bulk hydrogel fails at one of the clamped edges. This behavior of the hydrogels breaking at the edges of adhered areas when portions of the hydrogel hangs off the edge of the substrate was commonly observed. The hydrogels do not exhibit adhesive failure, but the failure force of approximately 0.18 N can be used to bound the adhesion strength with a lower limit of 1.8 kPa.

The invention claimed is:

1. An adhesive hydrogel comprising a (co) polymer matrix, wherein the adhesive hydrogel comprises at least one rough surface that includes at least one feature having a height of from about 50 micrometers to about 200 micrometers measured perpendicular to a plane in which the adhesive hydrogel lies,
the rough surface having a topography characterized as being a peak-valley topography,
the (co) polymer matrix comprising any one or more of (i) a homopolymer or a copolymer of 2-hydroxyethyl methacrylate, (ii) a homopolymer of poly(ethylene glycol) diacrylate or of poly(ethylene oxide), (iii) a copolymer of poly(ethylene glycol) diacrylate or of poly(ethylene oxide), (iv) a homopolymer or a copolymer of poly(propylene oxide), (v) a homopolymer of a copolymer of poly(acrylic acid), (vi) a homopolymer or a copolymer of poly(vinyl alcohol), or (vii) a polysaccharide-based (co) polymer,
wherein the topography of the rough surface is randomly arranged, and
wherein valleys of the peak/valley topography form a randomly-arranged network of microchannels that allow fluids to drain from contact points between a substrate when contacted to the adhesive hydrogel.

2. The adhesive hydrogel of claim 1, wherein the adhesive hydrogel further comprises at least one smooth surface.

3. The adhesive hydrogel of claim 1, wherein the adhesive hydrogel comprises two rough surfaces.

4. The adhesive hydrogel of claim 3, wherein each of the two rough surfaces are situated on opposites sides of the adhesive hydrogel to each other.

5. The adhesive hydrogel of claim 1, wherein the (co) polymer matrix comprises a homopolymer or copolymer of 2-hydroxyethyl methacrylate.

6. The adhesive hydrogel of claim 5, wherein the (co) polymer matrix comprises a copolymer of 2-hydroxyethyl methacrylate and poly(ethylene glycol) diacrylate.

7. The adhesive hydrogel of claim 2, wherein the root mean square roughness of the at least one rough surface is at least one order of magnitude higher than the root mean square roughness of the at least one smooth surface.

8. The adhesive hydrogel of claim 1, wherein the (co) polymer concentration is less than 32 weight %, based on the total weight of the adhesive hydrogel.

9. The adhesive hydrogel of claim 1, wherein the (co) polymer concentration is from 28 to 32 weight %, based on the total weight of the adhesive hydrogel.

10. The adhesive hydrogel of claim 1, wherein the (co) polymer matrix comprises N-isopropyacrylamide 2-(dimethylamino)ethyl methacrylate.

11. A process for preparing the adhesive hydrogel of claim 2, comprising the steps of:
(1) providing a reaction mixture comprising at least one monomer and water;
(2) charging a container comprising a smooth interior surface with a volume of the reaction mixture, such that the volume of the reaction mixture is less than the volume of the container; and
(3) covering the charged container with a lid and polymerizing the at least one monomer in the presence of the water to obtain the adhesive hydrogel comprising at least one rough surface and at least one smooth surface.

12. A process for preparing the adhesive hydrogel of claim 3, comprising the steps of:
(1) providing a reaction mixture comprising at least one monomer and water;
(2) charging a container comprising a rough interior surface with a volume of the reaction mixture, such that the volume of the reaction mixture is less than the volume of the container; and
(3) covering the charged container with a lid and polymerizing the at least one monomer in the presence of the water to obtain the adhesive hydrogel comprising two rough surfaces.

* * * * *

UNITED STATES PATENT AND TRADEMARK OFFICE
CERTIFICATE OF CORRECTION

PATENT NO. : 12,404,431 B2
APPLICATION NO. : 16/636967
DATED : September 2, 2025
INVENTOR(S) : Daeyeon Lee et al.

It is certified that error appears in the above-identified patent and that said Letters Patent is hereby corrected as shown below:

In the Specification

Under Column no. 4, Line no. 31, Replace:
"N-isopropyacrylamide"
With:
--N-isopropylacrylamide--

In the Claims

Under Column no. 10, Claim 10, Line no. 40, Replace:
"N-isopropyacrylamide"
With:
--N-isopropylacrylamide--

Signed and Sealed this
Fourteenth Day of October, 2025

John A. Squires
*Director of the United States Patent and Trademark Office*